(12) United States Patent
Neubauer

(10) Patent No.: US 9,199,013 B2
(45) Date of Patent: Dec. 1, 2015

(54) DEVICE FOR WOUND TREATMENT AND A WOUND COVERING BANDAGE OR DRESSING

(75) Inventor: Norbert Neubauer, Halberstadt (DE)

(73) Assignee: Simex Medizintechnik GMBH, Dreisslingen-Lauffen (DE)

( * ) Notice: Subject to any disclaimer, the term of this patent is extended or adjusted under 35 U.S.C. 154(b) by 0 days.

(21) Appl. No.: 13/704,962

(22) PCT Filed: Jun. 15, 2011

(86) PCT No.: PCT/DE2011/001866
§ 371 (c)(1),
(2), (4) Date: Dec. 17, 2012

(87) PCT Pub. No.: WO2012/041296
PCT Pub. Date: Apr. 5, 2012

(65) Prior Publication Data
US 2013/0090616 A1    Apr. 11, 2013

(30) Foreign Application Priority Data
Jun. 16, 2010    (DE) ..................... 20 2010 009 148 U

(51) Int. Cl.
*A61M 1/00* (2006.01)
*A61F 13/00* (2006.01)
(Continued)

(52) U.S. Cl.
CPC ........ *A61M 1/0056* (2013.01); *A61F 13/00068* (2013.01); *A61F 13/02* (2013.01);
(Continued)

(58) Field of Classification Search
CPC ........... A61F 13/02; A61F 2013/00174; A61F 2013/00246; A61F 2013/00412; A61F 2013/00536; A61F 5/441; A61F 2013/00251; A61F 2013/00255; A61F 2013/00259; A61F 2013/00263; A61F 2013/00268; A61F 2013/0054; A61F 2013/00855; A61F 2013/00859; A61M 1/0056; A61M 1/0088; A61M 1/0092; A61M 27/00; A61M 2205/7536; A61M 2001/00; A61M 2001/0031; A61M 2001/0033; A61M 2001/0035; A61M 2001/0088; A61M 2001/0092; A61M 2039/205; A61M 2202/0014; A61M 2202/02; A61M 2205/7518; A61M 2205/7527; A61M 2210/04; B65D 2205/00; B65D 2205/025; B65D 2205/02; B65D 51/1616; B65D 85/8043
See application file for complete search history.

(56) References Cited

U.S. PATENT DOCUMENTS 2,507,375 A * 5/1950 Hartwell ................... H04R 1/12
                                                               379/421
3,952,727 A * 4/1976 Nolan ........................... 604/333
(Continued)

FOREIGN PATENT DOCUMENTS

DE    692 29 940        3/2000
DE    698 25 767        9/2005
(Continued)

OTHER PUBLICATIONS

Porvair Filtration Group specification sheet, p. 19. http://www.porvairfiltration.com/UserFiles/File/PFG717_Fluorofil_Validation_Guide.pdf. Accessed Tuesday, Jun. 24, 2014.*

*Primary Examiner* — Adam Marcetich
(74) *Attorney, Agent, or Firm* — Levisohn Berger LLP

(57) ABSTRACT

A conventional wound covering bandage, which completely covers the wound area in an airtight, is provided with at least one opening located over the wound area, on which a stack of layers is provided, which comprises at least a filter disk, at least one paper-like disk which allows vapor diffusion but is water-impermeable, and at least one further flexible film, likewise having an opening, the flexible film and the bandage being superposed with respect to one another and the opening in the flexible film being in registry with the opening in the bandage. The flexible film covers and seals off all the aforementioned stack of layers by adhering to a face of the water-impermeable disk and a border area on a face of bandage circumscribing the stack of layers. The water-impermeable disk seals off the layer stack on the side facing the outside air.

2 Claims, 2 Drawing Sheets

(51) Int. Cl.
  A61F 13/02 (2006.01)
  A61M 27/00 (2006.01)
  B65D 51/16 (2006.01)
  A61F 5/441 (2006.01)
  B65D 77/22 (2006.01)
  B65D 85/804 (2006.01)

(52) U.S. Cl.
  CPC .......... *A61M 1/0088* (2013.01); *A61M 1/0092* (2014.02); *A61M 27/00* (2013.01); *B65D 51/1616* (2013.01); *A61F 5/441* (2013.01); A61F 2005/4415 (2013.01); A61F 2013/0054 (2013.01); A61F 2013/00174 (2013.01); A61F 2013/00246 (2013.01); A61F 2013/00251 (2013.01); A61F 2013/00255 (2013.01); A61F 2013/00259 (2013.01); A61F 2013/00412 (2013.01); A61F 2013/00536 (2013.01); A61F 2013/00855 (2013.01); A61F 2013/00859 (2013.01); A61F 2013/00863 (2013.01); A61M 1/0031 (2013.01); A61M 1/0033 (2014.02); B65D 77/225 (2013.01); B65D 85/8043 (2013.01)

(56) References Cited

U.S. PATENT DOCUMENTS

| | | | | |
|---|---|---|---|---|
| 4,274,848 A * | 6/1981 | La Gro | ................. | 96/6 |
| 4,318,406 A * | 3/1982 | McLeod | ................. | 604/333 |
| 4,427,425 A * | 1/1984 | Briggs et al. | ................. | 96/12 |
| 4,449,970 A * | 5/1984 | Bevan et al. | ................. | 604/333 |
| 4,490,145 A * | 12/1984 | Campbell | ................. | 604/333 |
| 4,512,771 A * | 4/1985 | Norton | ................. | 604/324 |
| 4,668,258 A * | 5/1987 | Steer | ................. | 96/12 |
| 5,056,510 A * | 10/1991 | Gilman | ................. | 602/52 |
| 5,136,640 A * | 8/1992 | Kim | ................. | H04R 1/12 379/439 |
| 5,203,764 A | 4/1993 | Libbey et al. | | |
| 5,636,643 A | 6/1997 | Argenta et al. | | |
| 5,645,081 A | 7/1997 | Argenta et al. | | |
| 5,693,035 A * | 12/1997 | Leise et al. | ................. | 604/333 |
| 6,506,184 B1 * | 1/2003 | Villefrance | ................. | 604/333 |
| 6,695,824 B2 | 2/2004 | Howard et al. | | |
| 7,857,806 B2 | 12/2010 | Karpowicz et al. | | |
| 2003/0004476 A1 * | 1/2003 | Kanbara | ................. | 604/333 |
| 2003/0100870 A1 * | 5/2003 | Villefrance | ................. | 604/333 |
| 2005/0015065 A1 * | 1/2005 | Falconer | ................. | A61F 5/441 604/335 |
| 2005/0028828 A1 | 2/2005 | Heaton et al. | | |
| 2006/0032372 A1 * | 2/2006 | Dauber et al. | ................. | 95/90 |
| 2007/0055205 A1 * | 3/2007 | Wright et al. | ................. | 604/174 |
| 2007/0219532 A1 | 9/2007 | Karpowicz et al. | | |
| 2008/0086996 A1 * | 4/2008 | Dougherty | ................. | 55/524 |
| 2009/0227969 A1 | 9/2009 | Jaeb et al. | | |
| 2009/0234307 A1 * | 9/2009 | Vitaris | ................. | A61M 1/0049 604/304 |
| 2009/0247970 A1 * | 10/2009 | Keleny et al. | ................. | 604/333 |
| 2010/0010460 A1 * | 1/2010 | Butler | ................. | 604/333 |
| 2010/0262095 A1 * | 10/2010 | Hall | ................. | A61M 1/0084 604/319 |
| 2010/0305524 A1 * | 12/2010 | Vess | ................. | A61M 1/0023 604/313 |
| 2011/0028918 A1 | 2/2011 | Hartwell | | |
| 2011/0224633 A1 * | 9/2011 | Robinson | ................. | A61M 1/0088 604/319 |
| 2011/0276016 A1 * | 11/2011 | Tsai | ................. | 604/319 |
| 2012/0296289 A1 | 11/2012 | Albert et al. | | |

FOREIGN PATENT DOCUMENTS

| | | |
|---|---|---|
| DE | 694 25 881 | 11/2005 |
| DE | 692 24 847 | 4/2007 |
| DE | 20 2009 016 141 | 4/2010 |
| EP | 1 764 127 | 3/2007 |
| WO | WO-2008/039314 | 4/2008 |
| WO | WO-2008/131895 | 11/2008 |
| WO | WO-2009/066106 | 5/2009 |

* cited by examiner

DEVICE FOR WOUND TREATMENT AND A WOUND COVERING BANDAGE OR DRESSING

BACKGROUND OF THE INVENTION

The invention relates to a device for wound treatment and a wound covering bandage or dressing made according to said device which advantageously can be used in particular in various methods for the vacuum wound treatment of surface wounds.

It is a frequent task in medical practice to suck off liquids. In particular, concerning deep, large and, in particular, additionally infected wounds. It is heretofore common practice to put wound covering onto the wound which does not grow together with the tissue. The medical puts a first mull layer upon this wound covering which a tube drain, partially in multiple turns is inserted by hand and the same in turn is covered by a second layer of mull and subsequently the entire wound area is covered by an adhesive plaster. A negative pressure is then applied to the end of the tube drain so that the wound liquid may be sucked off in this manner. Apart from the long period of time required to change the above described means this kind of procedure requires considerable skill because during the wound dressing all the separately put in parts of the arrangement have to be fixed which very often cannot be managed by a single person alone.

Another kind of wound covering which was particularly developed for wound treatment by vacuum is, for example, described in DE 601 18 546 T2. The wound covering described there requires, on the one hand, comparatively high manufacturing expenses and, on the other hand, it cannot be easily adapted to wounds of different size. In order to carry out a vacuum treatment this solution requires, among other things, relatively complicatedly executed additional coverings and, usually, a bell-shaped closure of the wound to which is applied an external vacuum connecter. Such designs which project far from the skin surface considerably restrict the movement of the patient and, in addition, cause an unpleasant pressure strain.

The above outlined treatment of such wounds to which a negative pressure is applied is a method practiced for many years which positively influences the healing also of deep and large wounds due to permanent wound stimulation. This kind of negative pressure wound treatment is, for example, described in detail in DE 694 25 881 T3, DE 692 29 940 T2, and DE 692 24 847 T3 so that herein only reference is made thereto. Furthermore, there exist numerous further solutions which will here only be mentioned by example since these are more remote technical solutions. So a wound dressing cover is known from U.S. Pat. No. 6,695,824 B2 for flat surface wounds which consists of two layers, the first layer being directly put upon the wound and the second layer having a moisture closure for preventing egress of moisture from outside the dressing. Between the layers a plurality of feed tubes are provided which ensure a moisture supply for the wound. The above mentioned wound dressing, however, is not designed and rather not suited for being used for wound treatment of deep and badly healing wounds with the aid of the technique of vacuum wound treatment, since it is practically impossible to bring out vacuum-tight from the wound area partially multiple turn tubes. The same applies to the numerous devices for sucking out the wound liquids from body cavities as described, for example, in EP 1 764 127 A1. Furthermore there is described a flat drainage in WO 2008/131895 A1 which eliminates the previously mentioned problem of sealing in that a flat drainage tail is led out laterally from under the dressing covering the wound.

From DE 698 25 767 T2 and DE 698 33 579 T2 there are suction heads known for wound treatment as well as a combination with a surgical sterile sheet in such a manner that a port with an adhesive bandage and a sucking off tube are adhered to a film which adheres to a wound. Here the hard port is disadvantageous which, when a vacuum is applied, presses upon the wound and thus causes pain.

Further applications also use such ports which only differ by different forms and materials as well as by different sucking channels.

Also here the hard port proves to be a disadvantage for the patient. Furthermore, the use of hard ports for small wounds is unsuited as concerns air circulation in the wound area, since a small adhesive face extending over the range of the wound will not be sufficiently aerated. Thus the sucking off of the wound liquid is impeded. The suction of the wound liquid may be maintained only by a special pump which enables the aeration of the wound via the suction tube.

Such special pumps with special additional aeration of the wound area are described, for example, in WO 2008/039314 A1, U.S. 2007/0219532 A1 and U.S. Pat. No. 7,857,806 B2. These, in fact, solve the problem of a continuous or discontinuous wound aeration while simultaneously maintaining the required negative pressure during the vacuum wound treatment, but there is the necessity of purchasing these at high costs. Furthermore, for example, the necessity of a second additional aeration connection within the wound area is expensive and unsuitable.

SUMMARY OF THE INVENTION

It is an object of the present invention to provide a device for vacuum wound treatment which can be used multimodally, even when commercially conventional vacuum pumps are used, and permits adequate ventilation of the wound when the negative pressure required in the wound area is reached, without complicated control means for the vacuum pump being necessary nor a respectively manufactured wound covering bandage.

The essence of the invention consists in that a part of a conventional wound covering bandages (i.e., adhesive bandage), which completely covers the wound area in an airtight manner with respect to the outside, is provided with at least one opening located over the wound area, on which a stack of layers is provided, which comprises at least one filter disk, in particular a bacterial filter disk, at least one paper-like disk which permits vapor diffusion but at the same time waterimpermeable, and at least one further flexible film, likewise having an opening which is arranged in the wound bandage in a manner corresponding to said one opening, said flexible film covers and seals off all the aforementioned layer pack constituents with the wound bandage directly or indirectly at the sides and in the border area in a sealing manner, wherein the at least one watertight disk is arranged in such a way that it seals off said layer stack on the side facing the outside air.

By selection of the porosity of the filter disk for which a great variety is for sale on the market, and by the capability to definedly select the respective diameters of the desired passage openings, the choke effects of the proposed device may be definedly adapted to the employed vacuum treatment procedures and the employed vacuum pumps.

When the proposed device is provided as an integral part of the wound covering, the operating surgeon can omit the additional steps for installing the same.

When the device is offered separately on a carrier film, the operating surgeon has only to provide the wound covering with an opening, the diameter of which has to be somewhat larger than the opening of the proposed invention which has to be placed on the former so to avoid that the preselected choke effect will not be changed. This can easily be done also by an inexperienced operator. The main advantage of the proposed device consists in that no changes have to be executed on the vacuum pump technology and on the vacuum pump method already tested successfully. Here, however is a time-delayed choke action preselectably adjustable over a wide range of the vacuum. Since an aeration of the wound via the pump itself does not take place, the danger of germs entering via the pump path is not any longer given.

When filters, in particular bacterial filters, have to be employed in the device according to the invention which are moisture-sensitive, not only the side of the layer stack facing the ambient air will be provided with a closing of a water-impermeable material disk or a disk with a moisture-repellent layer, which also functions as a water-impermeable disk, but also the side of the inventive device adjacent to the wound will be provided with such a closing layer.

The invention will be explained in more detail hereinafter by virtue of special examples of embodiment.

BRIEF DESCRIPTION OF THE DRAWINGS

There is schematically shown in:

FIG. 1 shows by virtue of a top plan view of the example according to FIG. 2 how the sectional views of FIGS. 2 to 6 have to be understood, namely as vertical sections along a plane (section line)X-X.

In FIG. 2 there is illustrated a first possible embodiment in which, at first and as common in prior art, a wound covering bandage 2 is attached to a schematically represented wound W. This wound covering bandage 2 hermetically seals the wound. Vacuum tubes, packing the wound W with mull, drainage means and so forth would also be present but are not shown for the sake of clarity. According to the present invention an opening 21 is made into the wound covering bandage 2 in this example, upon which a filter disk 11 is arranged, in particular formed by a bacterial filter having a diameter of about 10 mm, upon which furthermore a paper-like disk 12 (preferably consisting of Tyvek ®) is provided which permits vapor diffusion, but, at the same time, is water-impermeable.

Figure 1:
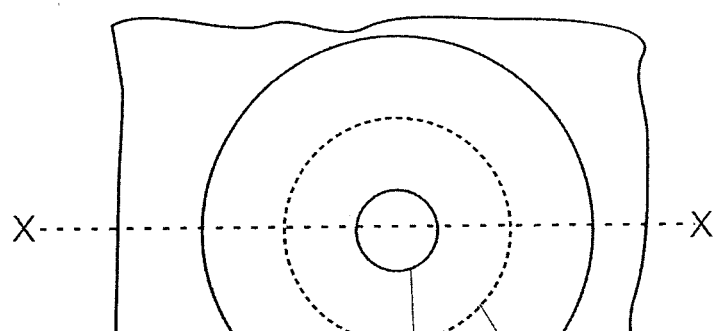
FIG. 1 a top plan view of general representation of a number of embodiments of the invention, the other figures being non-scale cross-sections taken on line X-X of FIG. 1.

The filter 11 and the disk 12 are enclosed by a sealing film 14, which is adhered to the top face of the disk 12 and, in a border area 15, to the bandage 2, and fixedly connected to the wound covering bandage 2. This can be effected by gluing or by welding, depending on the material of the wound covering bandage and of the film. In the film 14 there is provided, in registry with the opening 21 in the wound covering bandage 2, also an air intake opening 141. In this example the openings 21 and 141 have the same diameter a and b.

Figure 2:
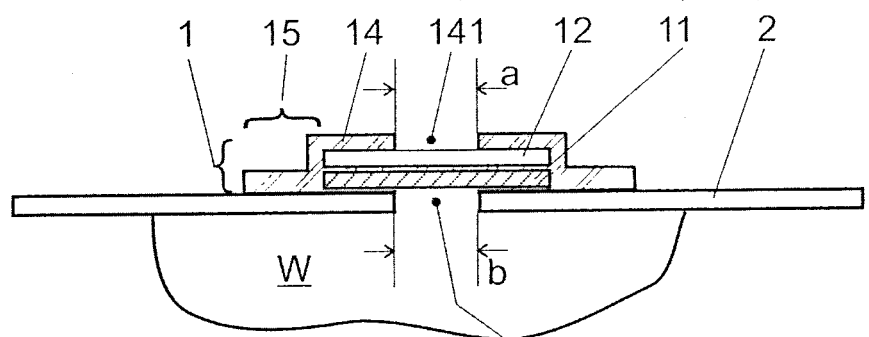
FIG. 2 a first embodiment in which the device according to the invention is provided directly upon a wound covering bandage.
Figure 3:
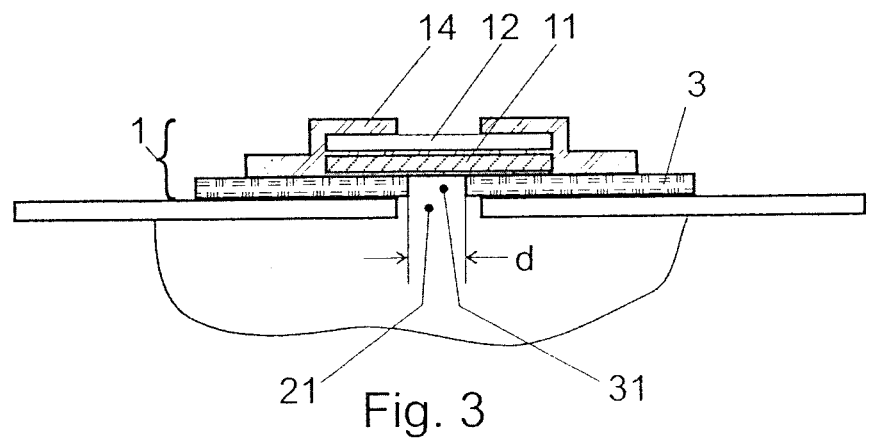
FIG. 3 a second embodiment in which the device according to the invention is arranged directly upon a separate carrier film which is provided above an opening in the wound covering bandage.

In FIG. 3 there is an embodiment shown identical to FIG. 2 with the exception that the filter 11, disk 12, and film 14 are provided on a separate carrier film 3, the face of which directed towards the wound covering bandage having an adhesive layer. After the operating surgeon has provided a flat intact wound covering bandage 2 with an opening 21, he will fix the device 1 of the invention, by help of said adhesive layer, over the opening 21 in such a manner that the opening 31 in the carrier film 3 registers with the opening 21 in the wound covering bandage 2. It is made apparent by this example that the opening 21 has to be always executed larger than the opening 31 in the carrier film 3 which together with the cross section of the choke determines the latter, the smaller diameter of the opening 31 being designated with d in FIG. 3, so that the choke properties determined before by the filter material, its thickness and permeability, will not affect the thickness of further components of the layer stack and so forth.

Figure 4:
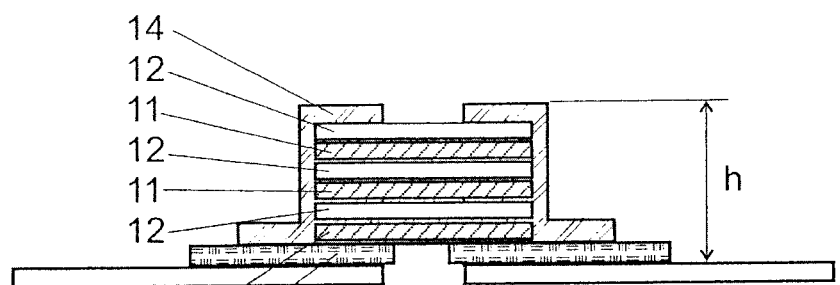
FIG. 4 an exemplary embodiment comprising a layer-stack in analogy to the example according to FIG. 3
Figure 5:
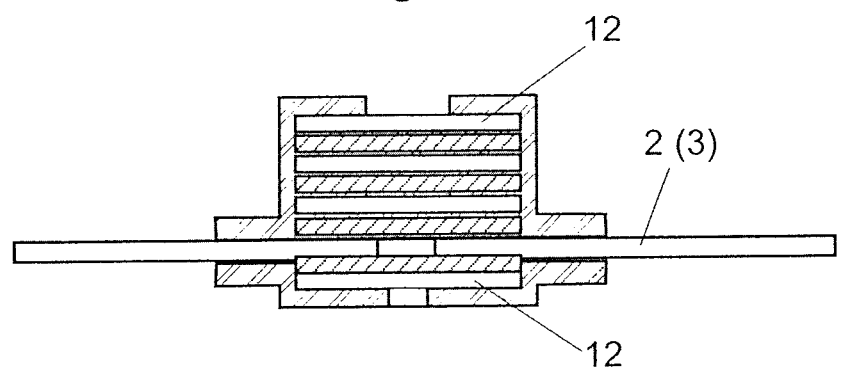
FIG. 5 an exemplary fourth embodiment in which the layer-stack provided according to the invention is divided and mounted on both faces of a wound covering bandage or upon a carrier film.

FIG. 4 only shows by example, that the layer stack 1 may also comprise a plurality of filter disks 11 of same or different properties and a plurality of disks 12, provided that the choke cross section requirements have to be satisfied. Even with such a setup as shown in FIG. 4 the entire height h of a device in this example only amounts to 1.3 mm. Due to the comparatively small diameters of the individual disks of the layer stack, a substantially flexible connection and fixation to the wound covering bandage 2 is ensured which, in contrast to the measures of the prior art do not affect the patient, in that, for example, additional pressure pains as common with the prior art do not occur anymore. In a fourth embodiment according to FIG. 5 the possibility is shown to split up the mentioned layer stacks and to arrange the same on both sides of a wound covering bandage 2 or of a carrier film 3. Even such an embodiment lies within the scope of the invention. By virtue of this FIG. it should particularly be made clear that it may be, for example, advantageous with intensively weeping wounds to provide at first a water-impermeable disk 12 on the wound side. The latter protects the filter 11 and prevents a possible blocking of the same, even when the direction of flow of the device by sucking outside air occurs in direction of the wound. It is not necessary to provide disks 12 within the entire layer-stack; in any case such a disk should cover and shut off the device towards the outside air so enabling the patient to take a shower without problems.

Figure 6:
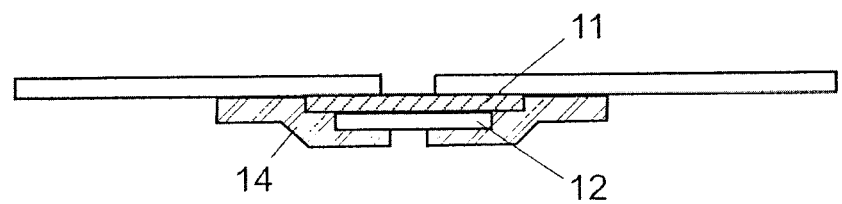
FIG. 6 exemplarily a fifth embodiment in the form of a stepped frustum of a cone of the disks which may be used in all the above embodiments.
Figure 7:
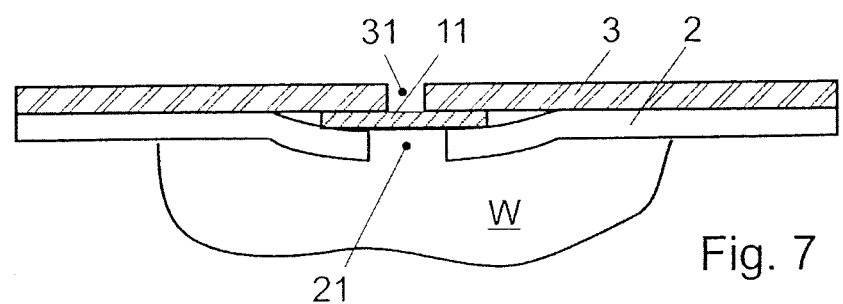
FIG. 7 is a sixth embodiment which a simple form of realization of the invention as well as the simplest form of realization of a wound covering plaster manufactured according to the present invention.

FIG. 6 illustrates by virtue of only two disks 11, 12 an advantageous embodiment in which the diameters of the filter disk 11 and of the waterproof paper-like disk 12 are stepwise tapering in such a manner that an arrangement design as a stepped frustum of a cone results having the disk of the smallest diameter adjacent to the disk at the respective outside. The smallest disk diameter has to be, of course, still greater than that of the opening lying above the larger disk. Such an embodiment simplifies when manufactured with the flexible film 14 attached which more securely retains the stack of disks. By extensive testing it was found that it is advantageous to provide the opening opposite to the wound with an opening diameter half as large as the opening towards the outside air. Thus diameters of the opening towards the outside air of from 6 mm up to 1 mm combined with selected diameters of the opening opposite to the wound of from 3 mm down to 0.5 mm, respectively, yielded positive test results in use. Finally, there should be still mentioned a most simple form of realizing the invention (FIG. 7), that is, when the user of the invention will do without the effect of the disk 12. Then a carrier film 3 provided with a one-sided adhesive layer will be employed into which an opening 31 of a preselectably defined diameter is provided. In this example only one filter disk 11 is glued directly over the opening 31. Said filter disk will be placed head-on directly over the opening 21 in the wound covering bandage 2, pressed on, and the carrier film 3 is directly connected to the wound covering bandage via the remaining adhesive layer which surrounds the filter disk and is not shown in FIG. 7. When a plurality of filters 11 and/or water-impermeable disks 12, as described hereinbefore, will be used also in such an embodiment, these firstly will be mutually fixed via their border areas before they will be, in an assembly with the carrier film 3, applied to the wound covering bandage 2, in which an opening 21 is provided, and air-tightly connected to the remaining surrounding area. The assembly produced in such a manner realizes then the function of the film 14 as described in the other embodiments.

Without being specially illustrated, still a further possibility within the scope of the invention should be referred to, namely, that at least one further detachable adhesive bandage having an opening of smaller diameter than the opening 141 in the film 14 is applied over the opening 141 facing the outside air. When the operating surgeon finds out that, when starting the vacuum pump, the aeration of the wound is inadequate, he only needs to remove said separate plaster of smaller diameter and thus increase the air-inlet cross-section.

The above given specifications of diameters for the openings provided do not limit the invention to circular cross-sections of the openings. Any other shape is feasible, provided that they are in accordance with the other specifications of the invention. Also, the arrangement of a plurality of separate openings in any of the described devices as well as providing a plurality of such devices upon large areas of wound covering bandages lies within the scope of the invention.

Finally, it the effects of the devices of the invention in use will be described. When a negative pressure is applied, the wound filling in the wound W, not shown here in the drawings, will be compressed, and the secretion flows from the wound W via the suction tubes, not shown either, as long as an air circulation exists in the wound. When, in particular, small wounds are concerned, the air circulation is according to the prior art only possible when the wound is aerated via pumps. When a pump without wound aeration is used, then such an inadmissible and painful negative pressure results after a short time that the pump is automatically switched off. This occurs already with wound diameters in the order of size of 50-70 mm. Now one had to wait, in order to be able to pump off wound secretion, so long until an aeration of the wound through the wound covering bandage itself occurs. Still more harmful would be aeration via the suction tubes, since these are contaminated by germs. When, however, the device according to the invention will be used, aeration will take place already after 12 to 15 sec. Thus it is ensured that, depending on the method of the vacuum wound treatment, a negative pressure of 200 mbar will not be exceeded, not even for a short time. The device according to the invention can be economically manufactured and can be employed with all known methods of vacuum wound treatments (even with pumps in intervals).

The invention claimed is:

1. A method of ventilating a wound area, comprising the steps of:
    covering said wound area with an adhesive bandage, whereby said adhesive bandage completely covers said wound area;
    forming an opening in said adhesive bandage covering said wound area;
    providing a separate carrier film having an underside surface and a second side, said underside surface of said separate carrier film comprising an adhesive layer, said separate carrier film further comprising an opening and a bacterial filter being larger than said opening in said separate carrier film adhered to said adhesive layer so as to cover said opening in said separate carrier film, whereby a segment of said adhesive layer surrounds said bacterial filter;
    connecting said separate carrier film to said adhesive bandage by way of said segment of said adhesive layer that surrounds said bacterial filter;
    whereby said step of connecting said separate carrier film to said adhesive bandage is performed after said step of covering said wound area with said adhesive bandage.

2. The method of claim 1, further comprising the step of placing said opening in said separate carrier film in registry with said opening formed in said adhesive bandage.

* * * * *